(12) United States Patent
Bao et al.

(10) Patent No.: US 11,530,174 B2
(45) Date of Patent: Dec. 20, 2022

(54) METHOD FOR ADSORPTION AND SEPARATION OF PROPYLENE, PROPYNE, PROPANE AND PROPADIENE

(71) Applicant: ZHEJIANG UNIVERSITY, Hangzhou (CN)

(72) Inventors: Zongbi Bao, Hangzhou (CN); Liangying Li, Hangzhou (CN); Qilong Ren, Hangzhou (CN); Zhiguo Zhang, Hangzhou (CN); Yiwen Yang, Hangzhou (CN); Qiwei Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/282,727

(22) PCT Filed: Oct. 24, 2019

(86) PCT No.: PCT/CN2019/113067
§ 371 (c)(1),
(2) Date: Apr. 2, 2021

(87) PCT Pub. No.: WO2020/093877
PCT Pub. Date: May 14, 2020

(65) Prior Publication Data
US 2022/0002217 A1 Jan. 6, 2022

(30) Foreign Application Priority Data
Nov. 9, 2018 (CN) .......................... 201811332100.9

(51) Int. Cl.
*C07C 7/12* (2006.01)
*B01D 53/02* (2006.01)
(Continued)

(52) U.S. Cl.
CPC ................ *C07C 7/12* (2013.01); *B01D 53/02* (2013.01); *B01J 20/226* (2013.01); *B01J 20/3071* (2013.01)

(58) Field of Classification Search
None
See application file for complete search history.

(56) References Cited

U.S. PATENT DOCUMENTS

| | | | |
|---|---|---|---|
| 2014/0224120 A1* | 8/2014 | Inubushi | B01D 53/02 502/402 |
| 2015/0144085 A1* | 5/2015 | Inubushi | F02B 43/02 546/5 |
| 2015/0165415 A1* | 6/2015 | Inubushi | B01J 20/226 95/96 |

FOREIGN PATENT DOCUMENTS

| | | |
|---|---|---|
| CN | 101454260 | 6/2009 |
| CN | 108727607 | 11/2018 |

* cited by examiner

*Primary Examiner* — Tam M Nguyen
(74) *Attorney, Agent, or Firm* — Jiwen Chen; Joywin IP Law PLLC

(57) ABSTRACT

The present invention discloses a method for separating propylene, propyne, propane and propadiene from mixed gas, wherein, comprising: a high purity component can be obtained as metal-organic frameworks as adsorbents through adsorptive separation and purification of a mixed gas containing propylene, propyne, propane and propadiene a general structural formula of the metal-organic framework material is $[M(C_4O_4)(H_2O)] \cdot 1.5H_2O$, wherein M is metal ions, the metal-organic framework material is a three-dimensional network structure formed by transition metal ions or alkaline earth metal ions and squaric acid through coordination bonds or intermolecular forces. The metal-organic framework materials of the present invention exhibit excellent adsorption and separation performances for propylene, propyne, propane and propadiene. The cheap and available (Continued)

raw materials for the synthesis, simple operation, and low cost make it cost-efficient for preparation of such metal-organic frameworks. Besides, the good regeneration and repeatability, the adsorption performances kept intact with that of the original one after being activated under vacuum for several times, indicating that they have a great promising and potential for industrial application.

7 Claims, 3 Drawing Sheets

(51) Int. Cl.
    *B01J 20/22*     (2006.01)
    *B01J 20/30*     (2006.01)

METHOD FOR ADSORPTION AND SEPARATION OF PROPYLENE, PROPYNE, PROPANE AND PROPADIENE

This is a U.S. national stage application of PCT Application No. PCT/CN2019/113067 under 35 U.S.C. 371, filed Oct. 24, 2019 in Chinese, claiming priority of Chinese Application No. 201811332100.9, filed Nov. 9, 2018, all of which is hereby incorporated by reference.

TECHNICAL FIELD

The present invention relates to the technical field of adsorption materials and energy sources, in particular to a method for adsorption separation of propylene, propyne, propane and propadiene.

BACKGROUND TECHNOLOGY

Propylene ($C_3H_6$) as the most basic chemical raw material has been widely used in the production of various chemicals. For example, the total production of polypropylene reached 85 million tons in 2013, second only to that of polyethylene. At present, propylene is generally obtained through the gas cracking of petroleum and multi-carbon hydrocarbons, but the cracked products are often complicated in composition, usually containing trace amounts (1000 to 2000 ppm) of propyne ($C_3H_4$) and propadiene. In order to obtain polymerization grade propylene for production, the amount of propyne and propadiene must be reduced to 5 ppm or even 1 ppm, but due to the similar structure and molecular dynamic size as well as extremely trace amount of propyne and propadiene among propylene stream, making it extremely challenging for the separation of propylene/propyne/propadiene.

Selective partial hydrogenation of propyne is the conventional method to remove the residual propyne from propylene stream in industry (such as Teschner D, Borsodi J, Wootsch A, et al. Science, 2008, 320(5872): 86-89.). However, noble metal catalysts such as a supported Pd catalyst are commonly used, which have some drawbacks including the need of noble metal catalysts and the loss of propylene due to the over hydrogenation to propyne or propadiene. The difference of relative volatility between propane and propylene is only 0.1, thus it is difficult to separate propane and propylene through the cryogenic distillation because of the extremely harsh conducted conditions, relative low temperature of 244-327 K and high pressure up to 1.7-30 bar. Moreover, about 200 trays are needed in the cryogenic distillation, an energy- and cost-extensive process. The huge energy consumption and the high requirement of the small- and pilot-scale equipment of cryogenic distillation limit its application in petrochemical industry. Therefore, there is still an urgent need to develop a more economical and energy-efficient technology for separation and purification of propylene, propyne, propane and propadiene. Adsorptive separation is an alternative method compared with cryogenic distillation due to its simple operation, low energy consumption as well as cost-efficient. However, design of an adsorbent with considerable adsorption capacity and high separation selectivity is vital for separation of propylene, propyne, propane, and propadiene. Commonly used adsorbents including activated carbon, clay, molecular sieves, silica gel, etc., are limited in the application for separation and purification of propylene because of their undesignable structure and low separation selectivity/uptake capacity.

The metal-organic framework materials, exhibiting high surface areas and pore volumes, are versatile owing to the exquisite control over synthesis condition, such as the types of metal ions and/or ligands and have displayed great potential for gas separation and purification. Separation of propylene and propyne has rarely been explored so far, such as Xing et al. (Yang L, Cui X, Yang Q, et al. Adv. Mater., 2018, 30(10): 1705374.) report some anion pillared materials, SIFSIX-1-Cu, SIFSIX-2-Cu-i, SIFSIX-3-Ni, SIFSIX-3-Zn, and NbOFFIVE-1-Ni that have highly efficient adsorption and separation performance for propyne/propylene. Based on the adsorption equilibrium, the formation of π-complexes between unsaturated hydrocarbons and open-metal sites is the most efficient method for propylene and propane separation. For example, MOF-74, MIL-100 and Cu-BTC, etc. (Bloch ED, Queen WL, Krishna R, et al. Science, 2012, 335(6076): 1606-1610. Yoon J W, Seo Y K, Hwang Y K, et al. Angew. Chem. Int. Ed., 2010, 49(34): 5949-5952. He Y, Krishna R, Chen B. Energy Environ. Sci., 2012, 5(10): 9107-9120.). Besides, depending on molecular size between the propyne and propylene is another efficient technology due to the different diffusion kinetics of these molecules within channels. For example, the ZIF-8 reported by the Li team enables the efficient separation of propylene/propyne through the difference in the diffusion of gas molecules in the material pores (Li K, Olson DH, Seidel J, et al. J. Am. Chem. Soc., 2009, 131(30): 10368-10369.).

However, most metal-organic framework materials exhibit poor hydrothermal stability and cost-intensive preparation not only for the expensive ligands but also for the large organic solvents used. For example, N,N-dimethyl Formamide or N,N-dimethylacetamide, etc. are highly involved in the preparation and further purification processes. It is still an urgent and challenging technology to develop and design metal-organic frameworks with high stability, uptake capacity and high separation selectivity for gas separation.

SUMMARY OF THE INVENTION

In order to overcome the problems existing in the prior art, the present invention provides a new application of a metal-organic framework material in the separation of propylene, propyne, propane and propadiene.

An application of a metal-organic framework material in the separation of propylene, propyne, propane and propadiene, a general structural formula of the metal-organic framework material is $[M(C_4O_4)(H_2O)] \cdot 1.5H_2O$, wherein M is metal ion.

A method for separation of propylene, propyne, propane and propadiene from mixed gas comprises the following steps:

Using a metal-organic framework material as an adsorbent, a single gas is obtained by adsorptive separation and purification from a mixed gas containing propylene, propyne, propane and propadiene; wherein a general structural formula of the metal-organic framework material is $[M(C_4O_4)(H_2O)] \cdot 1.5H_2O$, wherein M is metal ion; the pores of the metal-organic framework material are square or rhombus, and the pore size is 3.2-4.5 angstroms.

The metal-organic framework material is a three-dimensional network structure formed by transition metal ions or alkaline earth metal ions and squaric acid through coordination bonds or intermolecular forces.

The adsorption and separation process of the present invention is simple, and the mixed gas under a certain pressure can be passed through an adsorption tower or an adsorption column filled with the adsorbent. Furthermore, the adsorption tower can also be composed of one or more components, and the existing pressure swing adsorption, vacuum pressure swing adsorption or temperature swing adsorption can be used to realize the separation.

Preferably, a temperature of adsorption and separation is −5~50° C., a total pressure of the mixed gas is 100~1000 kPa. More preferably, a temperature of adsorption and separation is 20~50° C., a total pressure of the mixed gas is 100~400 kPa. Most preferably, a temperature of adsorption and separation is 25° C., a total pressure of the mixed gas is 100 kPa.

Preferably, the metal ion is selected from calcium, molybdenum, chromium, iron, cobalt, nickel, copper, magnesium or manganese ions. More preferably, the metal ion is selected from calcium, cobalt or nickel.

Preferably, the shape of the metal-organic framework material is cube, rod, particle or stick.

The adsorption mechanism of the present invention is: the pores of the metal-organic framework material are square or rhombus, and the pore size is 3.2-4.5 angstroms, which is very close to the molecular size of the target gas molecules, suggesting a good separation effect. When alkali is added as a reaction reagent, the hydroxyl groups as template have participated to construct the structure of the metal-organic framework materials, leading to a polarization of the pore chemistry. The higher polarizability of gas molecules can enter and be adsorbed firmly in the polar channels, suggesting that a strong interaction between the polar hydroxyl groups and gas molecules. And a weaker interaction could be similarly formed between the lower polarizability and polar groups. There is a significance difference of uptake capacity between these gas molecules due to the thermodynamic combined with kinetic influences. When the mixed gas passes through the adsorption tower, the one with lower uptake capacity and weaker affinity first elute from the adsorption tower quickly, while the adsorbed firmly and with higher uptake capacity gas molecule needs a long retention time to be eluted. Thus the high-efficiency adsorption and separation is achieved on this material.

Preferably, the metal-organic framework material is prepared by the following method:

(1) mixing an inorganic salt, a squaric acid, an alkali, and a deionized water in proportion, stirring and dissolving, and putting them into a normal pressure or high-pressure reactor for reaction; the inorganic salt is chloride, nitrate, acetate, carbonate, sulfate or perchlorate of the metal ion.

(2) after the hydrothermal reaction, it is washed with deionized water several times, and then dried in vacuum.

In the preparation process of the metal-organic framework material, the squaric acid is used as an organic ligand and coordinates with a series of metal inorganic salts in pure water without the use of toxic and volatile organic solvents. The inexpensive raw materials, mild synthesis condition, simple operation, and easy post-treatment reveal that the preparation of this material is cost-efficient. In the method of the present invention, the metal-organic framework materials not only exhibit high adsorption and separation selectivity for propadiene and propyne over propylene and propane, but also display an excellent chemical and water stability, demonstrating a great promising and potential for industrial application.

After the adsorbent used in the present invention is saturated with adsorption, the adsorbent can be regenerated at 25~150° C. under vacuum or helium inert atmosphere for 10~48 hours. The structure of the adsorbent will be collapsed as the temperature is too high or the time is too long. On the contrary, the adsorbent could not be fully regenerated with a lower temperature or shorter time compared with the former one.

The adsorbent prepared by the above-mentioned preferred method in the present invention has stable structure, regular particle shape, suitable pore size, and high selectivity as well as considerable adsorption capacity for the adsorption and separation of propylene, propyne, propane and propadiene.

Preferably, the molar ratio of the inorganic salt, squaric acid and alkali is 1:(0.5~3):(0~5). Water acts as a solvent and is evaporated in the subsequent drying process. Further preferably, when the inorganic salt is a cobalt salt, a nickel salt or a molybdenum salt, the molar ratio of the inorganic salt, squaric acid and alkali is 1:(1~1.5):(2~4). when the inorganic salt is a calcium salt, the amount of alkali added is 0, and the molar ratio of the inorganic salt and squaric acid is 1:1.

The crystal size, shape, regularity, and etc. will be changed accordingly with the ratio of metal salt, squaric and alkali changed, which could have a noticeable influence for the separation performance of propyne, propadiene, propylene, and propane. Most preferably, when the inorganic salt is a calcium salt, the alkali amount is 0. Besides, the molar ratio of the inorganic salt and squaric acid is 1:1.

Most preferably, the inorganic salt is cobalt chloride, and the molar ratio of the inorganic salt, squaric acid and alkali is 1 mmol:1.5 mmol:4 mmol.

The stirring step is: stirring at 500 to 1000 revolutions/minute for a propriate time to mix the solution uniformly. Inhomogeneous mixing will result in irregular crystal forms obtained by the reaction.

Further preferably, the reaction temperature of the hydrothermal reaction is 100-220° C., and the reaction time is 12-112 hours. Further preferably, the reaction is 120-220° C. for 24-100 hours. The reaction temperature affects the formation of crystals, and too high or too low will result in failure to generate crystals.

The product after the hydrothermal reaction is washed and centrifuged with water several times to replace the residual ligand, alkali solution and residual inorganic salt in the pores.

More preferably, the temperature of vacuum drying is 25 to 150° C., and the time is 10 to 24 hours.

Preferably, the mixed gas is not limited to containing propylene, propyne, propane and propadiene, but may also contain other gases such as carbon dioxide, methane, helium, argon, oxygen and the like. The raw material gas of the present invention has a wide composition range, various concentrations can be applied, and the content of each gas can range from 5% to 85%.

The metal-organic framework materials used in the present invention can be molded into spherical, columnar, particle and other adsorption separation materials through different processing techniques or made into membrane materials according to the existing conventional technology for membrane separation of propylene, propyne, propane and propadiene.

Compared with the prior art, the present invention has the following advantages:

The metal salt used in the preparation of the metal-organic framework material involved in the present invention is rich in nature, especially calcium carbonate which is abundant in mineral reserves. The organic ligand squaric acid is cheap and easy to obtain. The synthesis conditions are mild, and the purification steps of samples are simple, so as easily to operate and scale-up. The metal-organic framework materials involved in the present invention exhibit stable structure and high adsorption selectivity for propylene/propyne/propane/propadiene. Besides, the adsorptive separation performances of these materials keep intact with the original one after several repeated adsorption-desorption cycles. In terms of the adsorption and separation of the mixed gas, the adsorbent prepared by the present invention is far superior to most solid adsorbents.

DETAILED DESCRIPTION OF THE INVENTION

Figure 1:
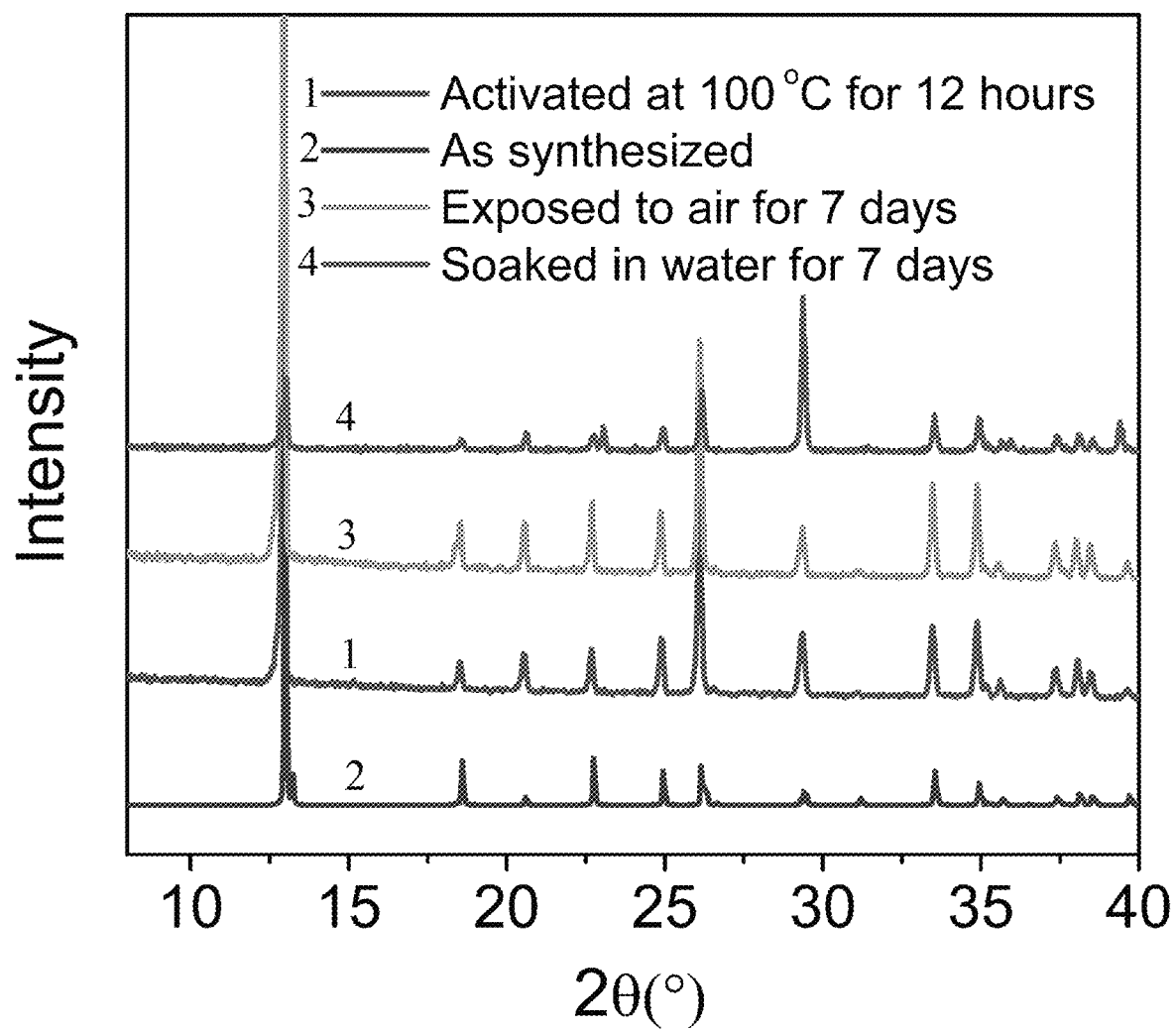
FIG. 1 is an XRD pattern of the stability investigation of the metal-organic framework material prepared in embodiment 1.

The following embodiments further illustrate the present invention, but the content of the present invention is not limited to these embodiments at all.

Embodiment 1

0.151 mmol calcium carbonate and 0.151 mmol squaric acid were added into 20 mL deionized water and stirred for 30 minutes before transferred into a 25 mL hydrothermal reactor. Then the reactor was kept at 120° C. for 24 hours. After the reaction was completed and cooled down, a purified metal-organic framework material was obtained after washed with pure water several times. Prior to gas adsorption experiments, the purified adsorbent was activated at 100° C. under vacuum for 12 hours to obtain the solvent-free samples.

The single-component adsorption isotherms of propylene, propyne, propane and propadiene were performed on the above adsorbent with an appropriate amount at 0° C. and 25° C. The adsorption capacities of propylene, propyne, propane, and propadiene were 2.9, 3.3, 2.7 and 3.5 mmol/g, respectively, at 0° C. and 1 bar. The adsorption capacities of propylene, propyne, propane, and propadiene were 1.3, 2.8, 0.3 and 3.0 mmol/g, respectively, at 0° C. and 0.01 bar. The adsorption capacities of various gas molecules on this material were significantly different, indicating that the material has a good adsorption and separation performance for these four gas molecules. The adsorption capacities of propylene, propyne, propane, and propadiene were 2.6, 3.1, 2,3, and 3.3 mmol/g, respectively, at 25° C. and 1 bar. The adsorption capacities of propylene, propyne, propane, and propadiene were 0.6, 2.6, 0.3 and 2.8 mmol/g, respectively, at 25° C. and 0.01 bar. According to IAST calculations, when the propylene/propane volume ratio was 50:50, the adsorption selectivity of the adsorbent for propylene/propane was 10.6 and 8.1 at 0° C. and 25° C., respectively, at 0.01 bar. When the propylene/propyne volume ratio was 50:50, the adsorption selectivity of the adsorbent for propyne/propylene was 52.1 and 26.0 at 0° C. and 25° C., respectively, at 0.01 bar. When the propane/propyne volume ratio was 50:50, the adsorption selectivity of the adsorbent for propyne/propane was 365.8 and 136.3 at 0° C. and 25° C., respectively, at 0.01 bar. When the propylene/propadiene volume ratio was 50:50, the adsorption selectivity of the adsorbent for propadiene/propylene was 25.2 and 16.3 at 0° C. and 25° C., respectively, at 0.01 bar.

In order to test the stability of the sample, the sample was exposed to air under a relative humidity of 60% for 7 days and immersed in pure water for 7 days before performing the PXRD measurements. The PXRD curves were shown in FIG. 1. From the results, whether it was immersed in water for 7 days or exposed to air with a relative humidity of 60% for 7 days, the PXRD of the samples were consistent with the original synthesized one, indicating the excellent stability of the material.

Embodiment 2

1.93 mmol cobalt chloride hexahydrate, 2.88 mmol squaric acid, and 7.72 mmol potassium hydroxide were added into 7 mL deionized water and stirred for 30 minutes. Then transferred into a 25 mL hydrothermal reactor and kept at 220° C. for 48 hours. After the reaction was completed and cooled down, a purified metal-organic framework material was obtained after washed with pure water several times. The purified adsorbent was degassed at 120° C. under vacuum for 12 hours to obtain a solvent-free adsorbent before the gas adsorption measurements.

Figure 2:
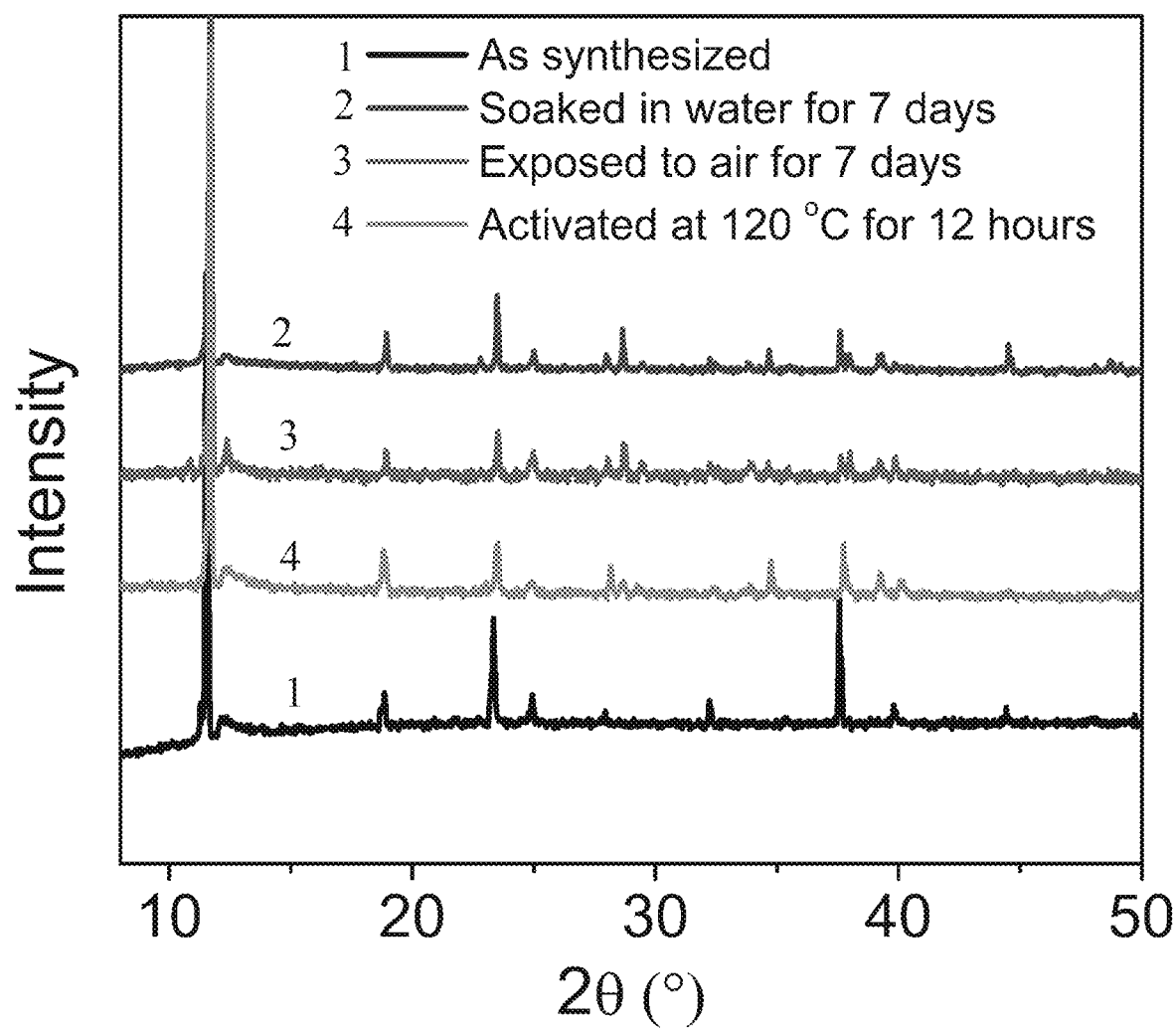
FIG. 2 is an XRD pattern of the stability investigation of the metal-organic framework material prepared in embodiment 2.

In order to test the stability of the sample, the sample was exposed to air under a relative humidity of 60% for 7 days and immersed in pure water for 7 days before PXRD measurements. The PXRD curves were shown in FIG. 2. From the results, whether it was immersed in water for 7 days or exposed to air with a relative humidity of 60% for 7 days, the PXRD of the samples were consistent with the original synthesized one, indicating the excellent stability of the material.

Embodiment 3

1.93 mmol nickel chloride hexahydrate, 2.88 mmol squaric acid and 7.72 mmol potassium hydroxide were added into 7 mL deionized water and stirred for 30 minutes. Then transferred into a 25 ML hydrothermal reactor and kept at 220° C. for 48 hours. After the reaction was completed and cooled down, a purified metal-organic framework material was obtained after washed with pure water several times. The purified adsorbent was degassed at 120° C. under vacuum for 12 hours to obtain a solvent-free adsorbent before the gas adsorption measurements.

Figure 3:
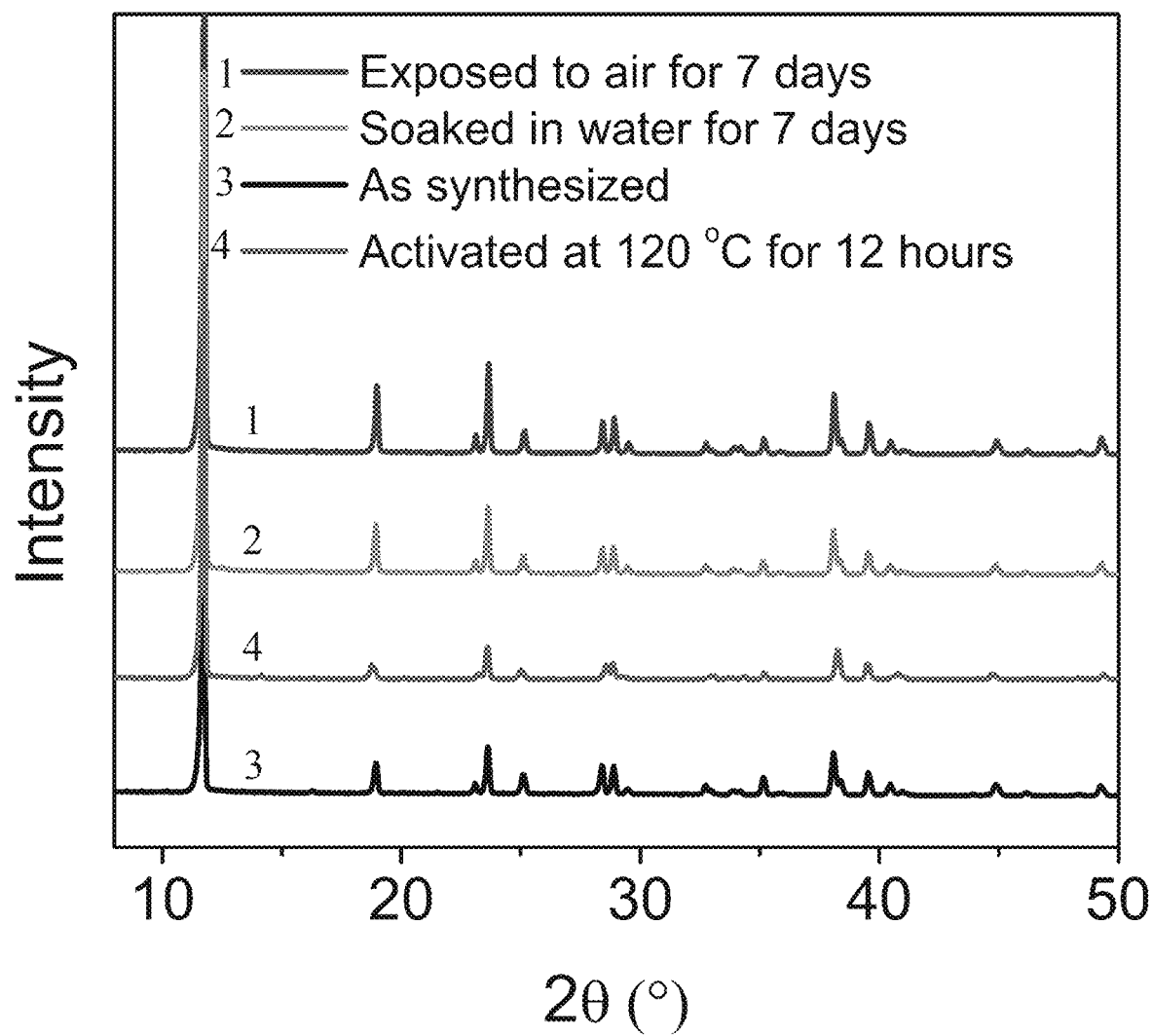
FIG. 3 is an XRD pattern of the stability investigation of the metal-organic framework material prepared in embodiment 3.

In order to test the stability of the sample, the sample was exposed to air under a relative humidity of 60% for 7 days and immersed in pure water for 7 days before the PXRD measurements. The PXRD curves were shown in FIG. 3. From the results, whether it was immersed in water for 7 days or exposed to air under a relative humidity of 60% for 7 days, the PXRD curves of the samples were consistent with the original synthesized one, indicating the excellent stability of the material.

The above are only specific implementation cases of the patent of the present invention, but the technical features of the patent of the present invention are not limited to this. Any changes or modifications made by those skilled in the relevant fields in the field of the present invention are all covered by the present invention. Within the scope of the patent.

The invention claimed is:

1. A method for separation of propylene, propyne, propane and propadiene from a mixed gas containing propylene, propyne, propane and propadiene, comprising the following steps:
   contacting an adsorbent with the mixed gas containing propylene, propyne, propane and propadiene; and
   obtaining propylene, propyne, propane and propadiene, respectively, by adjusting temperature or pressure for adsorption and separation;
   wherein the adsorbent is a metal-organic framework material;
   wherein a general structural formula of the metal-organic framework material is $[M(C_4O_4)(H_2O)] \cdot 1.5H_2O$; and
   wherein M is metal ion; pores of the metal-organic framework material are square or rhombus, and the pore size is 3.2-4.5 angstroms.

2. The method according to claim 1, wherein, the temperature for adsorption and separation is −5~50° C.

3. The method according to claim 1, wherein, a total pressure of the mixed gas is 100~1000 kPa.

4. The method according to claim 1, wherein, the metal ion is selected from calcium, molybdenum, chromium, iron, cobalt, nickel, copper, magnesium or manganese ions.

5. The method according to claim 1, wherein, the shape of the metal-organic framework material is cube, rod, particle or column.

6. The method according to claim 1, wherein, the metal-organic framework material is prepared by the following method:
   (1) mixing an inorganic salt, a squaric acid, an alkali, and a deionized water in proportion to form a mixture, stirring and dissolving, and putting the mixture into a normal pressure or high pressure reactor for reaction; the inorganic salt is chloride, nitrate, acetate, carbonate, sulfate or perchlorate of the metal ion; and
   (2) after the hydrothermal reaction, washing with deionized water several times, and then drying in vacuum.

7. The method according to claim 6, wherein, the molar ratio of the inorganic salt, squaric acid and alkali is 1:(0.5~3):(0~5).

* * * * *